Reissued Sept. 1, 1953 Re. 23,705

UNITED STATES PATENT OFFICE 23,705

DIAGNOSTIC COMPOSITIONS

Jonas Kamlet, New York, N. Y., assignor to Miles Laboratories, Inc., Elkhart, Ind., a corporation of Indiana No Drawing. Original No. 2,418,033, dated March 25, 1947, Serial No. 701,403, October 5, 1946. Application for reissue July 1, 1953, Serial No. 366,082

5 Claims. (Cl. 252—408)

Matter enclosed in heavy brackets [ ] appears in the original patent but forms no part of this reissue specification; matter printed in italics indicates the additions made by reissue.

The present invention relates to diagnostic compositions and, more particularly, to diagnostic compositions suitable for the qualitative detection and quantitative estimation of reducing carbohydrates (e. g., glucose, levulose, arabinose) in body fluids (e. g., urine, cerebrospinal fluid, milk). It has for its object to provide a simple, rapid and convenient method for performing these tests with a high degree of accuracy and without the necessity of employing an extraneous source of heat, such as a gas burner, alcohol lamp or ignited hexamethylenetetramine tablet.

The present application is a continuation-in-part of my copending applications, Serial No. 343,777 filed July 3, 1940, and Serial No. 500,558, filed August 30, 1943.

The qualitative and quantitative estimations of glucose in urine are at present the best means available to the physician for controlling his diabetic patients. The daily dosage of insulin is usually determined by the presence or absence of glucose in the fasting urine, and, in the majority of diabetic patients, such a determination must be performed at least once daily. This is usually done by the patient himself.

Methods heretofore available were based on the principle of heating a mixture of measured aliquots of urine and an alkaline copper solution (such as Benedict's, Fehling's, Folin-McEllroy) or an alkaline bismuth solution (such as Nylander, Almen). In qualitative estimations, the precipitation of cuprous oxide from the cupric compound, in the former case, or the reduction of the bismuth ion to black metallic bismuth, in the latter case, would indicate the presence of a reducing carbohydrate.

In quantative estimations, the usual method employed heretofore has been that of Benedict (Journal of the American Medical Association, vol. 57, page 1193, 1911). This involves adding measured amounts of urine to an aliquot of a standard solution, while boiling the latter, until the blue cupric compound contained therein is completely decolorized, forming cuprous thiocyanate. By a calculation, the percentage of reducing substance in the urine is determined.

Sheftel, United States Patent No. 1,769,862, has described a method for the quantitative determination of sugar in urine based on the following steps: (a) Measured aliquots of a special modified Benedict solution containing creatinine and a hydrophile colloid are mixed with a measured aliquot of urine; (b) the mixture is heated in boiling water for five minutes; (c) if a change in the original blue color appears, the solution is compared with a color scale and the corresponding percentage of sugar is estimated.

All of the procedures thus mentioned have one great drawback. They all require an extraneous source of heat. It is obvious that a diabetic going about his daily business, or a military physician in the field, or a physician at his patient's bedside, cannot always have a gas burner available. Attempts to heat water by igniting hexamethylenetetramine tablets are usually futile.

Since the reduction of cupric ions to the cuprous form by glucose is effected only at advanced temperatures, it is the further purpose of this invention to provide dry, solid, alkaline, cupric ion-containing, compositions which will dissolve in urine with a strongly exothermic reaction, and which will be reduced to cuprous oxide if glucose or any other reducing carbohydrate is present in the urine. This will be effected without recourse to any extraneous source of heat.

The basis of all diagnostic solutions containing alkaline cupric ions heretofore employed is: (a) a cupric salt, such as cupric sulfate; (b) an alkaline-reacting substance, such as sodium carbonate, or potassium hydroxide; (c) a member of the group of normal salts that are capable of holding cupric hydroxide in solution. Fehling (Annalen, vol. 72, page 106, of 1849) used normal alkali-metal tartrates (Rochelle salts), while Benedict (J. Biol. Chem. vol. 3, page 101, of 1907) used normal alkali-metal citrates and Folin-McEllroy (J. Biol. Chem. vol. 33, page 513, of 1918) used normal alkali-metal phosphates, pyrophosphates and thiocyanates.

I have found that stable diagnostic compositions of excellent specificity for reducing carbohydrates, and fulfilling the objects of the present invention, may be obtained by preparing solid, dry mixtures of the following ingredients in proper proportions:

(a) A water soluble cupric salt.

(b) A solid alkali material of the group consisting of the oxides and hydroxides of the alkali metals, and (c) A member of the group of solid acids and acid reacting salts forming water-soluble complexes with cupric ions in alkaline solution, which group consists of citric acid, tartaric acid, the alkali metal acid salts of citric [and tartaric acids, the alkali metal and alkaline-earth metal hemibasic and monobasic salts of orthophosphoric acid, and the alkali metal and alkaline-earth metal dibasic salts of pyrophosphoric] acid.

Preferably, for convenience of the user, the dry mixtures are tableted so that each tablet will be sufficient to make one diagnostic determination. When these compositions, either in powder or tablet form, are mixed with a small amount of an aqueous specimen such as urine, they dissolve rapidly with the evolution of a considerable amount of heat. It may be desirable to dilute the urine specimen with water. In the absence of a reducing carbohydrate, a clear blue solution is obtained. In the presence of a reducing sugar, a green, yellow or brownish red precipitate of cuprous oxide is obtained, which is held in suspension by the highly concentrated alkaline solution. To determine quantitatively the amount of reducing carbohydrate present in the urine specimen, the color of the suspension may be compared with the panels of a standard color chart of known concentrations of glucose (or other reducing carbohydrates) in urine (or any other specimen being tested).

In accordance with Beer's law, on which the entire art of colorimetry is based, the intensity of the observed color of the precipitate is directly proportional to the concentration of the colored substance (i. e., cuprous oxide). However, since the concentration of the cuprous oxide is also directly proportional to the concentration of reducing carbohydrates originally present in the specimen, the observed color is likewise directly proportional to the concentration of the reducing substance.

If desired, diluents, excipients, and ancillary or auxiliary agents may be incorporated into the dry diagnostic compositions. Thus, a minor proportion of an alkali metal bicarbonate (e. g., sodium bicarbonate) may be added. When the dry diagnostic composition containing such a bicarbonate is added to the liquid specimen being tested, the solid acid or acid reacting salt therein will interact with the alkali metal bicarbonate liberating gaseous carbon dioxide. The effervescence thus produced serves to accelerate the mechanical disintegration of the composition, especially if it is in tablet form. The reaction is thus speeded up, and the determination is effected more promptly. Since the total heat evolution is thereby effected within a shorter period, there is less loss of heat by radiation, conduction and vaporization, and traces of reducing carbohydrates are detectable, which might otherwise go undetected.

A desiccating agent, such as calcium chloride, and diluents and excipients, such as kaolin and talc, may be employed without adversely affecting the sensitivity and specificity of the diagnostic compositions. Auxiliary agents, such as creatinine and the hydrophilic colloids, may be incorporated, their presence in the test solution being advised by Sheftel, to prevent the formation of the red form of cuprous oxide.

Typical examples of ingredients from group (a) above that may be used (i. e., water soluble cupric salts) in preparing the diagnostic compositions are cupric sulphate, cupric chloride, and cupric acetate.

Typical examples of members of group (b) (i. e., oxides and hydroxides of alkaline metals) that may be used in the diagnostic compositions are sodium hydroxide and potassium hydroxide. Although lithium oxide and hydroxide are more expensive than the other members of this group, their use in some compositions may be justified by reason of their comparatively low hygroscopicity. Sodium and potassium hydroxides are the preferred hydroxides since their heats of solution are more than double that of lithium hydroxide. Likewise, sodium and potassium oxides both have considerably higher heats of solution than lithium oxide.

Typical examples of ingredients of group (c) (i. e., solid acids and acid reacting salts which form water soluble complexes with cupric ions in alkaline solution) that may be used in preparing the dry diagnostic compositions are: citric acid (monohydrate) *and,* tartaric acid [and hemibasic sodium orthophosphate $NaH_2PO_4.H_3PO_4$].

The following example[s] of *a* typical composition[s] covered by this invention [are] *is* intended to define and illustrate, but in no way to limit the invention to the particular reagents or proportions described therein. [These] *This* composition[s] may be used in the form of powder, or dispensed in pellets, or [they] *it* may be pressed into unitary reaction tablets of such a size as is convenient for the performance of a single test.

Example [I]

One kilogram of finely powdered caustic soda is thoroughly mixed with 500 grams of citric acid (monohydrate) and 50 grams of anhydrous cupric sulfate, until the mixture is homogeneous. It is then pressed into five grain tablets.

To perform a test, a tablet is placed into a test-tube and 0.5 cc. of urine is added dropwise. A vigorous reaction occurs and the tablet dissolves in the urine with the evolution of considerable heat. In the presence of 0.075% or more of glucose in the urine, a suspension of cuprous oxide will be observed in the tube. The color of this suspension may be compared with that of a standard color chart to obtain an estimation of the amount of glucose present.

The sensitivity of this composition is about 0.075% of glucose, 0.125% of lactose and 0.135% of arabinose.

Similarly, these compositions are quite specific for reducing carbohydrates. Chloroform, uric acid, creatinine and albumin do not interfere with this test as they do in the case of the Fehling test and the Nylander reaction.

[Example II]

[Two kilograms of sixty mesh powdered caustic soda are thoroughly mixed with 200 grams of powdered anhydrous monobasic sodium orthophosphate and 20 grams of anhydrous cupric sulfate, until the mixture is homogeneous. It is then compressed into five grain unitary reaction tablets.]

[To perform a test on a suspected urine, a tablet is dropped into a round bottomed test tube containing five drops of the urine and 10 drops of water. A vigorous reaction occurs and the tablet dissolves in the urine with the evolution of considerable heat. In the presence of 0.050% or more of glucose in the urine a suspension of cuprous oxide will be observed in the tube. The color of this suspension may be compared with that of the panels of a standard color chart to obtain an estimation of the amount of glucose present.]

[The sensitivity of this composition is about 0.050% of glucose, 0.080% of lactose and 0.080% of arabinose. Similarly, these compositions are quite specific for reducing carbohydrates. Chloroform, uric acid, creatinine and albumin do not interfere with this test, as they do in the case of the Fehling test and the Nylander reaction.]

[Example III]

[Two kilograms of sixty mesh powdered caustic soda are thoroughly mixed with 176 grams of powdered hemibasic sodium orthophosphate and 20 grams of anhydrous cupric sulfate, until the mixture is homogeneous. It is then compressed into five grain unitary reaction tables.]

[These tablets are used in the manner described in Example II. The sensitivity and specificity are equally as good as those described in Example II.]

[Example IV]

[Two kilograms of sixty mesh powdered caustic soda are thoroughly mixed with 180 grams of powdered dibasic sodium pyrophosphate (sodium acid pyrophosphate), 20 grams of powdered sodium bicarbonate and 20 grams of anhydrous cupric sulfate, until the mixture is homogeneous. It is then compressed into five grain unitary reaction tablets, which are effervescent in use.]

[These tablets are used in the manner described in Example I. The sensitivity and specificity are equally as good as those described in Example I.]

[Example V]

[Two kilograms of sixty mesh powdered caustic soda are thoroughly mixed with 200 grams of powdered anhydrous hemibasic calcium orthophosphate, 30 grams of sodium bicarbonate and 25 grams of anhydrous cupric sulfate, until the mixture is homogeneous. It is then compressed into five grain unitary reaction tablets, which are effervescent.]

[Example VI]

[Two kilograms of caustic potash chips are thoroughly mixed with 180 grams of monobasic calcium orthophosphate monohydrate crystals and 20 grams of anhydrous cupric chloride, until the mixture is homogeneous. It is then compressed into five grain unitary reaction tablets.]

[Example VII]

[Two kilograms of anhydrous powdered lithium hydroxide are mixed with 250 grams of powdered monobasic potassium orthophosphate, 25 grams of sodium bicarbonate, 25 grams of anhydrous cupric sulfate and 50 grams of powdered talc, until the mixture is homogeneous. It is then compressed into five grain unitary reaction tablets.]

[Example VIII]

[Two kilograms of powdered dibasic sodium acid pyrophosphate are thoroughly mixed with 700 grams of powdered sodium oxide ($Na_2O$), 20 grams of powdered sodium bicarbonate and 20 grams of anhydrous cupric sulfate, under the scrupulous exclusion of moisture, until the mixture is homogeneous. It is then compressed into five grain unitary reaction tablets.]

Upon dissolution in water, the above composition is alkaline, and generates sufficient heat for the formation of cuprous oxide.

Because of the hygroscopicity of compositions within the scope of this invention, it is desirable, although by no means imperative, to use anhydrous reagents instead of the corresponding hydrates. Thus anhydrous cupric sulfate yields more stable compositions than the hydrate salt[.] [Anhydrous monobasic sodium orthophosphate is preferable to the hydrate], and this [preference] *greater stability* holds for all of the ingredients having two forms of high and low (or no) water content. However, if a hydrate does not have a tendency to deliquesce as the temperatures encountered in the localities where these compositions are to be used, it may be used in a preparation of the present invention. [Hemibasic sodium orthophosphate is particularly useful in this connection, in that it forms no hydrate.]

The heat evolved during the reaction of the diagnostic compositions of this invention with urine, or similar specimens, is predominantly due to two exothermic reactions. One of these is the heat of solution of the alkali metal oxide, or hydroxide, in the aqueous fluid. The other is the heat of neutralization of the solid acid or acid reacting salt with the alkali metal hydroxide in solution. The heat evolved will more than suffice to effect the reduction of the cupric complex to cuprous oxide, which forms a precipitate of characteristic color.

The dry diagnostic compositions may be used for the qualitative detection and quantitative estimation of reducing carbohydrates other than glucose. Thus, they may be used to detect pentosuria, to estimate the amount of galactose in urine during a galactose tolerance test for [depatic] *hepatic* function or hyperthyroidism, or the amount of lactose in milk.

I claim:

1. A diagnostic composition in solid dry form comprising a mixture of ingredients reactive when contacted with an aqueous liquid specimen containing reducing sugar to form cuprous oxide by action of the sugar on a material supplied by the mixture said ingredients comprising essentially: a minor quantity of a water soluble solid cupric salt; a solid acidic material selected from the group consisting of citric acid, tartaric acid, an alkali metal acid salt of citric acid, [an alkali metal acid salt of tartaric acid, an alkali metal monobasic orthophosphate, an alkali metal dibasic pyrophosphate, an alkali metal hemibasic orthophosphate, an alkaline-earth metal monobasic orthophosphate, an alkaline-earth metal dibasic pyrophosphate, and an alkaline-earth metal hemi-basic orthophosphate;] and a quantity of solid alkali material selected from the group consisting of alkali metal oxides and alkali metal hydroxides, the said alkali being present in excess of that required to neutralize the solid acidic material in the mixture and in an amount adequate to generate sufficient heat to form said cuprous oxide.

2. A diagnostic composition in solid dry form comprising a mixture of ingredients reactive when contacted with an aqueous liquid specimen containing reducing sugar to form cuprous oxide by action of the sugar on a material supplied by the mixture, said ingredients comprising essentially a minor quantity of a water soluble solid cupric salt, a quantity of solid citric acid, and a quantity of solid alkali material selected from the group consisting of alkali metal oxides and alkali metal hydroxides, the said alkali material being present in excess of that required to neutralize the solid citric acid in the mixture and in an amount adequate to generate sufficient heat to form said cuprous oxide.

3. A diagnostic composition in solid dry form comprising a mixture of ingredients reactive when contacted with an aqueous liquid specimen containing reducing sugar to form cuprous oxide by action of the sugar on a material supplied by the mixture, said ingredients comprising essentially a minor quantity of a water soluble solid cupric salt, a quantity of solid tartaric acid, and a quantity of solid alkali material selected from the group consisting of alkali metal oxides and alkali metal hydroxides, the said alkali material being present in excess of that required to neutralize the solid tartaric acid in the mixture and in an amount adequate to generate sufficient heat to form said cuprous oxide.

[4. A diagnostic composition in solid dry form comprising a mixture of ingredients reactive when contacted with an aqueous liquid specimen containing reducing sugar to form cuprous oxide by action of the sugar on a material supplied by the mixture, said ingredients comprising essentially a minor quantity of a water soluble solid cupric salt, a quantity of solid hemibasic sodium orthophosphate, and a quantity of solid alkali material selected from the group consisting of alkali metal oxides and alkali metal hydroxides, the said alkali material being present in excess of that required to neutralize the hemibasic sodium orthophosphate in the mixture, and in an amount adequate to generate sufficient heat to form said cuprous oxide.]

5. A diagnostic composition in solid dry form comprising a mixture of ingredients reactive when contacted with an aqueous liquid specimen containing reducing sugar to form cuprous oxide by action of the sugar on a material supplied by the mixture, said ingredients comprising essentially a minor quantity of solid cupric sulfate, a quantity of solid citric acid, and a quantity of solid sodium hydroxide, the latter being present in excess of that required to neutralize the citric acid in the mixture and in an amount adequate to generate sufficient heat to form said cuprous oxide.

6. A diagnostic composition in solid dry form comprising a mixture of ingredients reactive when contacted with an aqueous liquid specimen containing reducing sugar to form cuprous oxide by action of the sugar on a material supplied by the mixture, said ingredients comprising essentially a minor quantity of solid cupric sulfate, a quantity of solid tartaric acid, and a quantity of solid sodium hydroxide, the latter being present in excess of that required to neutralize the tartaric acid in the mixture, and in an amount adequate to generate sufficient heat to form said cuprous oxide.

[7. A diagnostic composition in solid dry form comprising a mixture of ingredients reactive when contacted with an aqueous liquid specimen containing reducing sugar to form cuprous oxide by action of the sugar on a material supplied by the mixture, said ingredients comprising essentially, a minor quantity of solid cupric sulfate, a quantity of solid hemibasic sodium orthophosphate, and a quantity of solid sodium hydroxide, the latter being present in excess of that required to neutralize the hemibasic sodium orthophosphate in the mixture, and in an amount adequate to generate sufficient heat to form said cuprous oxide.]

MILES LABORATORIES, INC.
By WALTER A. COMPTON,
*Vice President.*

No references cited.